(12) United States Patent
Volker

(10) Patent No.: US 9,962,481 B2
(45) Date of Patent: May 8, 2018

(54) TRANSPORT CARRIAGE FOR FLUSH SOLUTIONS

(71) Applicant: Manfred Volker, Blankenbach (DE)

(72) Inventor: Manfred Volker, Blankenbach (DE)

( * ) Notice: Subject to any disclaimer, the term of this patent is extended or adjusted under 35 U.S.C. 154(b) by 0 days. days.

(21) Appl. No.: 14/950,228

(22) Filed: Nov. 24, 2015

(65) Prior Publication Data

US 2016/0193402 A1    Jul. 7, 2016

(30) Foreign Application Priority Data

Nov. 25, 2014 (DE) ........................ 10 2014 017 397

(51) Int. Cl.
| | | |
|---|---|---|
| A61B 1/12 | (2006.01) | |
| A61B 90/70 | (2016.01) | |
| A61M 3/02 | (2006.01) | |
| A61M 5/14 | (2006.01) | |

(52) U.S. Cl.
CPC ........... *A61M 3/0233* (2013.01); *A61B 1/125* (2013.01); *A61B 90/70* (2016.02); *A61M 5/14* (2013.01); *A61M 5/1414* (2013.01); *A61M 2005/1402* (2013.01); *A61M 2005/1403* (2013.01)

(58) Field of Classification Search
CPC ...... A61B 1/125; A61B 90/70; A61M 3/0233; A61M 5/14; A61M 5/1414; A61M 2005/1402; A61M 2005/1403
USPC ..... 134/166 C, 166 R, 167 C, 167 R, 168 C, 134/168 R, 169 A, 169 C, 169 R, 170, 134/171; 141/313; 210/636
See application file for complete search history.

(56) References Cited

U.S. PATENT DOCUMENTS

| | | | |
|---|---|---|---|
| 6,096,007 A | 8/2000 | Haan et al. | |
| 7,635,359 B2 | 12/2009 | Nakazawa et al. | |
| 2006/0276762 A1* | 12/2006 | Nakazawa .......... | A61M 1/0001 604/319 |
| 2008/0027409 A1* | 1/2008 | Rudko ................... | A61B 5/201 604/503 |
| 2011/0042202 A1 | 2/2011 | Pettee et al. | |

FOREIGN PATENT DOCUMENTS

| | | |
|---|---|---|
| DE | 1955538 | 12/1966 |
| DE | 3315031 A1 | 1/1985 |
| DE | 4121568 A1 | 10/1992 |
| DE | 4122171 A1 | 1/1993 |
| DE | 4137748 A1 | 5/1993 |
| DE | 4332070 A1 | 3/1995 |
| DE | 69318988 T2 | 3/1996 |
| DE | 19538818 | 4/1997 |
| DE | 19733278 A1 | 2/1999 |
| DE | 102009057562 A1 | 6/2011 |

(Continued)

OTHER PUBLICATIONS

U.S. Appl. No. 14/950,218.

(Continued)

*Primary Examiner* — Levon J Shahinian

(74) *Attorney, Agent, or Firm* — Greer, Burns & Crain, Ltd.

(57) ABSTRACT

The transport carriage for flush solutions is characterized in that the flush solution is received in a flexible flush solution bag that is arranged in a rigid container, wherein a pressurized gas can be introduced into the flush solution bag or the rigid container.

6 Claims, 6 Drawing Sheets

(56) References Cited

FOREIGN PATENT DOCUMENTS

| | | |
|---|---|---|
| DE | 102010055781 A1 | 6/2012 |
| DE | 102011102662 A1 | 11/2012 |
| DE | 102012001879 A1 | 8/2013 |
| EP | 2689790 | 7/2012 |
| EP | 2674399 | 12/2013 |
| WO | 2005077335 A1 | 8/2005 |

OTHER PUBLICATIONS

U.S. Appl. No. 14/950,237.
U.S. Appl. No. 14/950,248.
U.S. Appl. No. 14/950,271.
U.S. Appl. No. 14/950,286.

\* cited by examiner

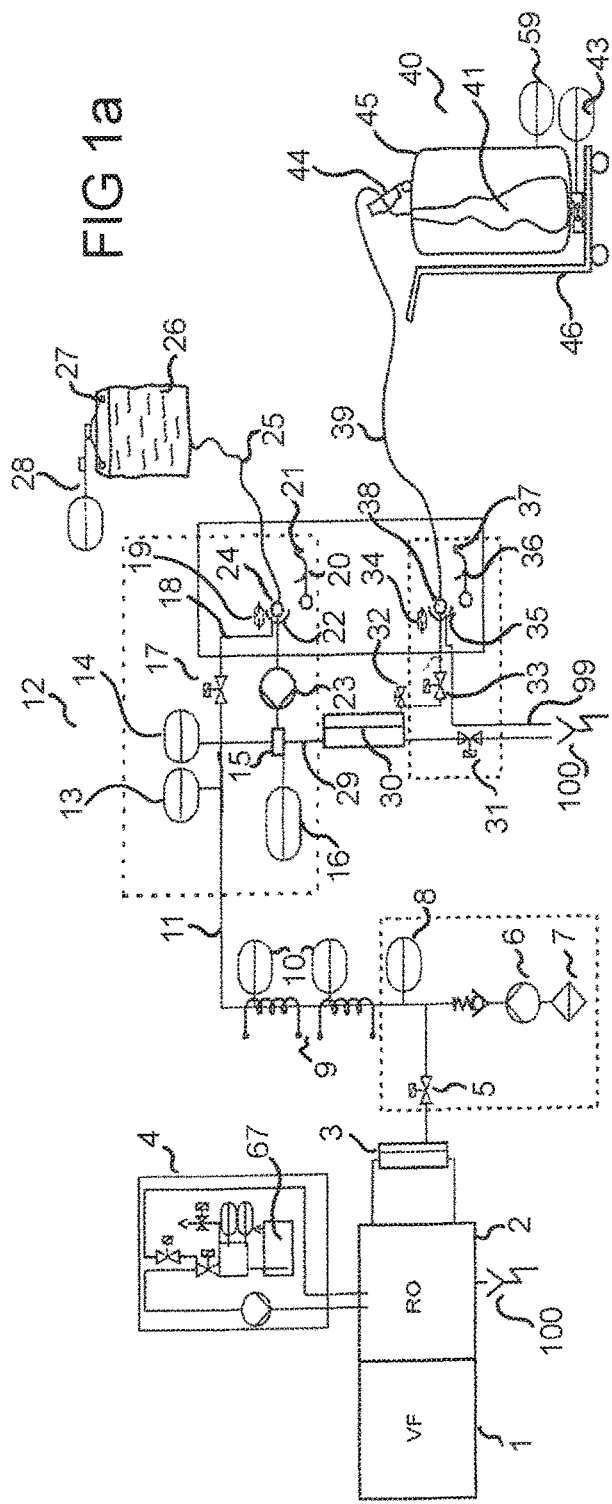

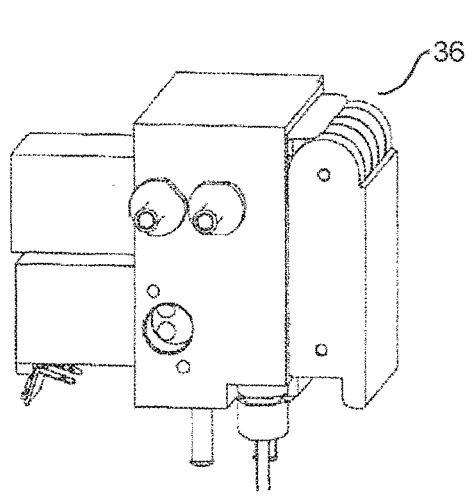
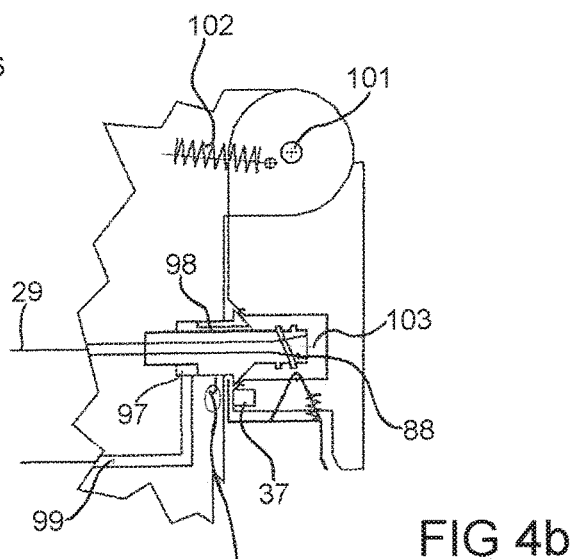
FIG 4a
FIG 4b
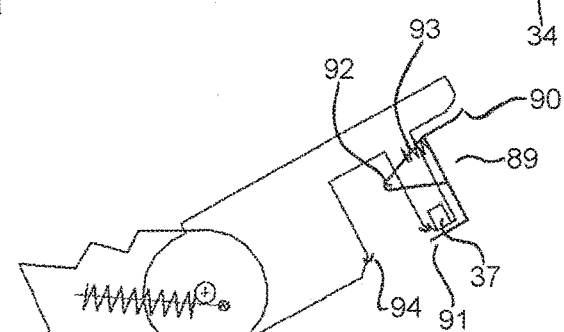
FIG 4c
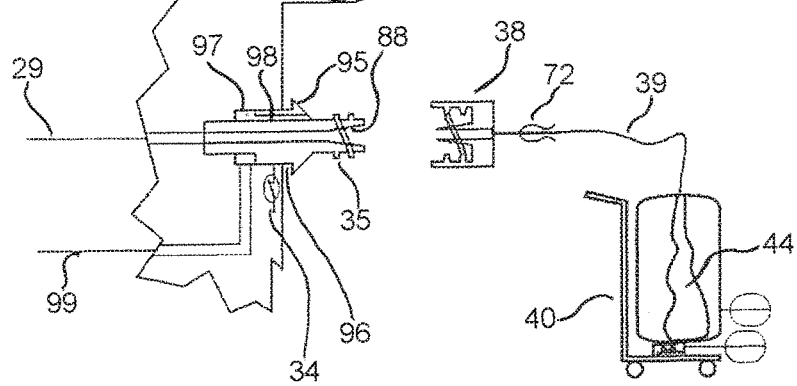

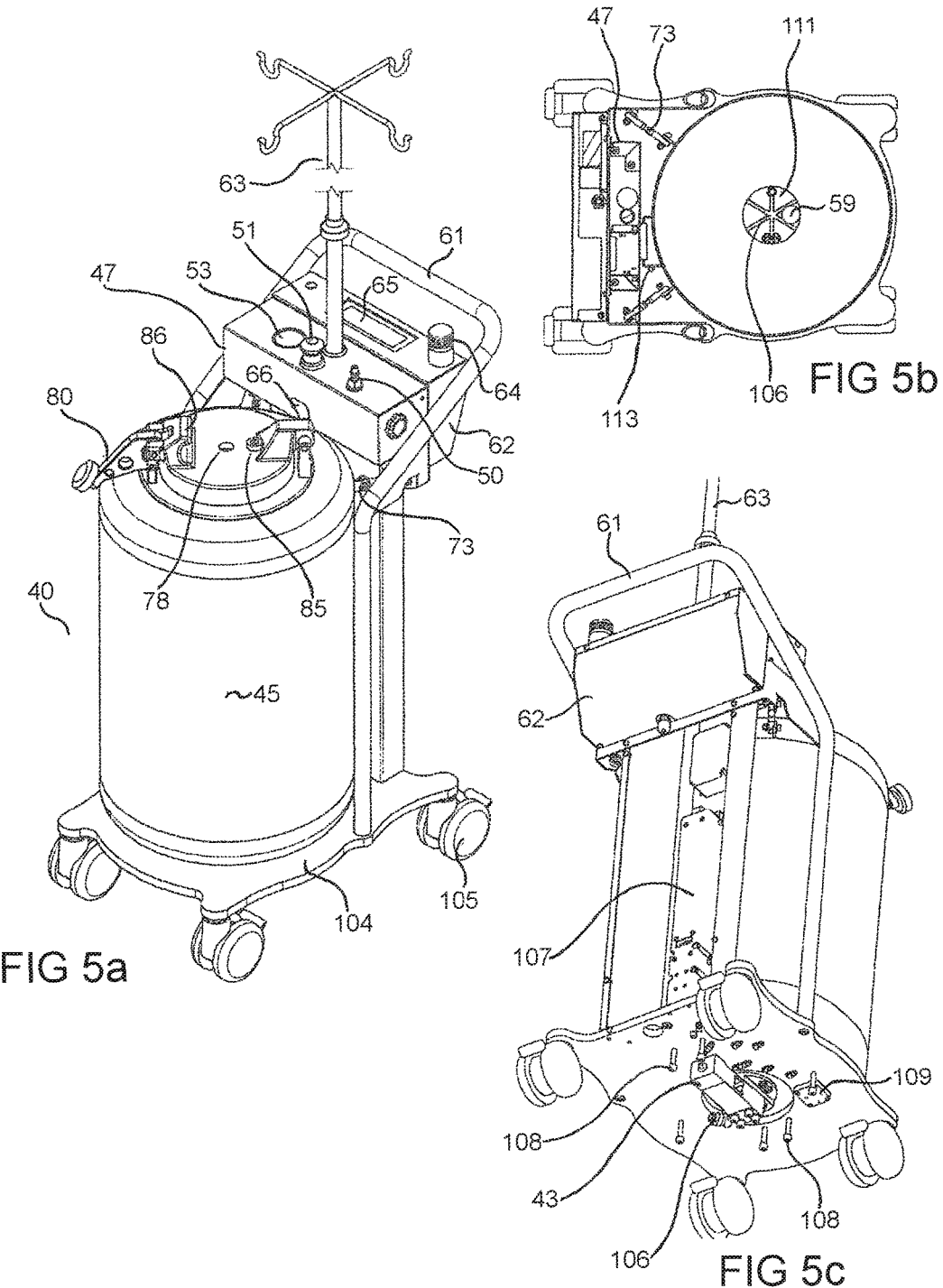

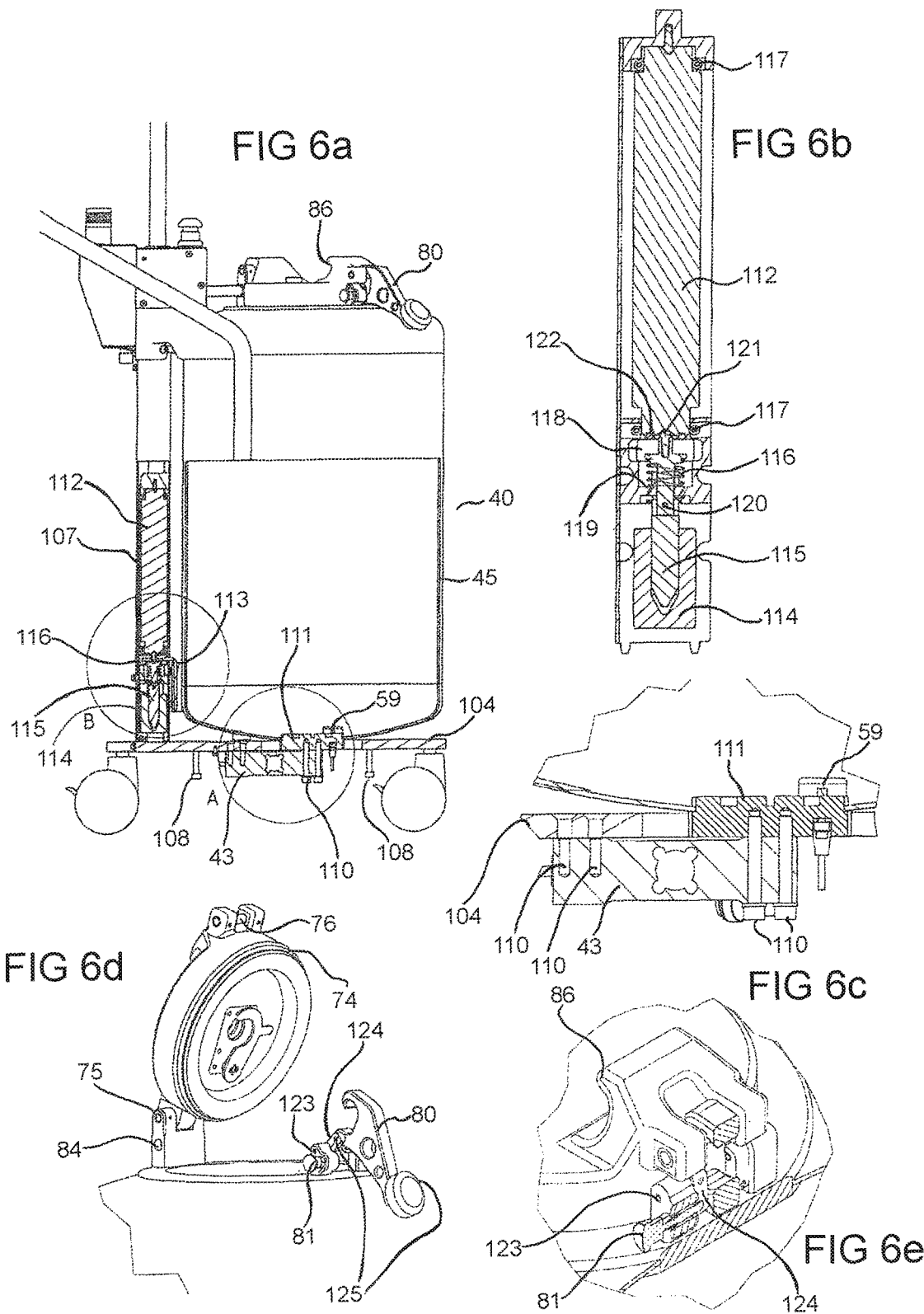

TRANSPORT CARRIAGE FOR FLUSH SOLUTIONS

FIELD OF THE INVENTION

The subject application relates to medical flushing solutions, and more particularly to a mixing unit for flushing solutions.

SUMMARY OF THE INVENTION

The objective of this development is to produce from tap water, through the use of filter technology, an economical, chemically and microbiologically high-purity fluid as a base substance for the use of medical flush solutions locally in a decentralized manner and to mix the same with a concentrate in such a manner that larger volumes of ready-to-use flush solutions are created that can be movably brought to the place of use and applied by means of pressurization.

In this process both flush solutions for endoscopic and general surgical operations, e.g., in gynecology, urology, arthroscopy through the use of Purisole, Ringer's, common salt concentrates, and also flush solutions for the relief of chronic illnesses or for therapeutic applications can be produced.

An application of this development to other areas such as, e.g., veterinary medicine, in the laboratory or in biology and pharmaceutics as a high-purity flush fluid or also as a base medium for the production of medicines, cell cultures and the like is conceivable and practicable.

As a rule, medical flush solutions are further processed into flush solutions in a central production process, taking as a base substance distilled water that is produced in a central process, whereby the flush solutions must then be brought to the place of use with considerable logistics costs.

For medical use, for example, industrially produced flush solutions with 3 l, 5 l and 10 l volumes are provided to the hospital and temporarily or permanently stored with substantial in-house, staff logistics operations.

These bag volumes are not sufficient for the duration of the operation or examination, for example, for bladder surgery with approximately 60-l flush fluid, so that a relief-person must be available outside the central OP area in order to provide, heat and hand over the bags.

Application is effected to some extent gravimetrically or also with pressure infusion cuffs. In addition, often expensive disposal articles such as, for example, pump segments or also bag warmers are required.

A crucial disadvantage during endoscopic examinations is the inability to see through free-floating tissue or pulsing flush fluid, because, for example, the required flush fluid pressure between 0.1 bar and 0.3 bar is not kept constant.

Generous flushing is necessary for an improvement in wound hygiene. This results in both personnel and material costs.

The regulative and normative requirements regarding the quality of the base substance water are thereby so high that until now it has not been possible to produce verifiable medical flush solutions locally, e.g., in a hospital, as needed.

On the one hand, it is the high microbiological requirements and, on the other hand, the necessary chemical requirements placed on the base substance water that stand in the way of verifiable and demonstrable, normative quality requirements of the local demand-driven production.

The decentralized production of medical flush solutions by hospital personnel demands reliable sequences both in the operation and also in the dependability of the technology with respect to the flush solution quality.

Necessary improvements, purpose and object of this invention are therefore an economical, user-friendly local production of a flush solution with low personnel deployment and a flush volume consistent with the examination or also with a plurality of operations.

Special significance is given to formula reliability, which means compliance with the prescribed composition, homogeneity, application temperature and hygiene of the solution.

A space-saving technology for the production of the flush solution and a mobile flush solution container should thereby be used, whereby said flush solution container contains the essential components for high hygiene, safety, simple operation and a constant flow and pressure for the application of the flush fluid.

A difficult to solve object is to minimize or preventively to reduce the rapid microbiological population within the filtering stages and water treatment on a sustained basis. Minimization and prevention are necessary because the filtering stages have only a certain level of germ retention from the primary side to the secondary side. Consequently water samples are therefore to be taken frequently and expensive microbiological tests are to be conducted as revalidation, as it were.

The required high availability of the devices during all measuring and monitoring tasks with respect to their intrinsic safety should thereby show only remote failure probability in order under all circumstances to avoid a catastrophic effect for the patient and perfectly to monitor the quality or also toxicity of the created fluid in the guaranteed acceptance criteria.

This object is effectively solved according to the invention by using the combination of a reverse osmosis membrane and two additional filtering stages, for example, ultra or sterile filters, preferably as capillary membrane, for the production of the flush solution.

This filter combination and further constituents are called the filling station in the following.

For example, for the production of approximately 60 l of ready-to-use Purisole solution, approximately 56 l of sterile-filtered permeate is to be proportionally diluted or mixed with approximately 3.6 l of highly concentrated Purisole concentrate in such a manner that the resulting flush solution can be used for intra- and post-operative bladder irrigation without additional testing.

This aforementioned flush solution is representative, e.g., for Ringer's and/or other sodium chloride solutions that can be used particularly in the field of surgery, but also in other medical or previously named areas, whereby the concentrates and their mixture ratios must be adapted.

In order to avoid the described disadvantages of the industrially manufactured, easily portable packaging sizes, preferentially volumes are provided that are adapted to the intended purpose and that are consequently usually not portable.

The described method and the components and volumes used are however not reduced to this. A large bandwidth of flush solutions can be produced conditional on the high-purity agents, exact mixing and dilution.

For homogenization and tempering, approximately sterile permeate is heated and mixed with metered-in concentrate in a mixing block.

Before the introduction into a sterile flush solution container/bag, a second sterile filtering of the mixed solution takes place.

The proportioning takes place by means of a concentrate scale and a flush solution container scale, whereby the concentrate scale is verified each time the filled concentrate container is hung on.

The object of filling that is correct with respect to the sterility, homogeneity and correct volume is solved in that with great advantage a mobile flush solution container, which is preferably formed as a pressurized container, is equipped with an insertable, sterile flush fluid bag.

For this purpose, with advantage the mobile flush solution container comprises a scale that monitors the filling level and that, for safety reasons, is to be automatically tested by means of a reference weight.

With the help of electronics that are operated by means of a rechargeable battery, the required parameters as well as their deviations, for example, weight, temperature and container pressure, can thereby be displayed on the mobile flush solution container.

By, for example, producing a wireless data exchange between the concentrate scale in the filling station and the container scale of the mobile flush solution container, among other units, monitoring of the proportionality and temperature, for example, is effected.

With great advantage, the flush solution bag contains a non-detachable link connector that can be stuck through the locking lid of the pressurized container and fixed in place. The link connector is provided with continuative flexible hose lines that are formed as filling or transfer lines.

The device-side links of both the concentrate bag and also of the flush solution bag are brought about by the user at self-cleaning, fool-proof link connectors of the filling station, which are executed in this application, for example, as flap solutions, but that can also be executed on the device side as flexible hose line.

For the application of the flush fluid at the place of use, a transition system is, at the transfer link of the flush solution connector, connected to an endoscopy system.

The object of simple operation and application with a constant flush flow and pressure is solved in that compressed gas (air) is either preferably introduced into the pressurized container or also selectively introduced directly into the flush fluid bag.

With advantage the compressed gas regulation and monitoring are thereby created within the mobile flush solution container. The feed-in can, for example, be produced by an in-house source, or also by the device.

The cleaning of the system or the germ prevention and reduction are executed by means of the combination of a slightly toxic disinfecting and cleaning agent based on citrate and by heating water, whereby both the primary and also the secondary side of the reverse osmosis are to be disinfected or cleaned, separately from one another, by means of an additional pump also without transmembrane flow.

In principle, all process-relevant data both from the operating computer and the protection computer are thereby acquired and, where appropriate, calculated. The measurement results are sent from the operating computer to the protection computer and from the protection computer to the operating computer. Each computer thereby compares the measurement results with its own and sends back a confirmation.

After the confirmation from the operating and protection computers, the data, together with a checksum, are written into the trend data memory, which can preferably be formed as EPROM, but also as some other storage medium.

Further details and advantages are described in the figures depicted in the following.

BRIEF DESCRIPTION OF THE DRAWINGS

FIG. 1a is a schematic view of flush fluid preparation system.

FIG. 1b is a schematic view of a possible transfer of flush fluid to an endoscopic system.

FIG. 4a is a perspective view of a concentrate valve.

FIG. 4b is a schematic cross-sectional view of the concentrate valve in a closed position.

FIG. 4c is a schematic cross-sectional view of the concentrate valve in an open position.

FIG. 5a is a perspective view of a container filling station.

FIG. 5b is a schematic view of a concentrate bag.

FIG. 5c is a detailed view of the concentrate bag connectors.

FIG. 6a is a vertical partial cross-sectional view of the container and transportation carriage.

FIG. 6b is a detail of circle B of FIG. 6a.

FIG. 6c is a detail of circle A from FIG. 6a.

FIG. 6d is an enlarged view of the container lid in an open position.

FIG. 6e is a detailed partial cross-sectional view of the lid locking device.

DETAILED DESCRIPTION OF PREFERRED EMBODIMENTS

Figures 2A, 2B:
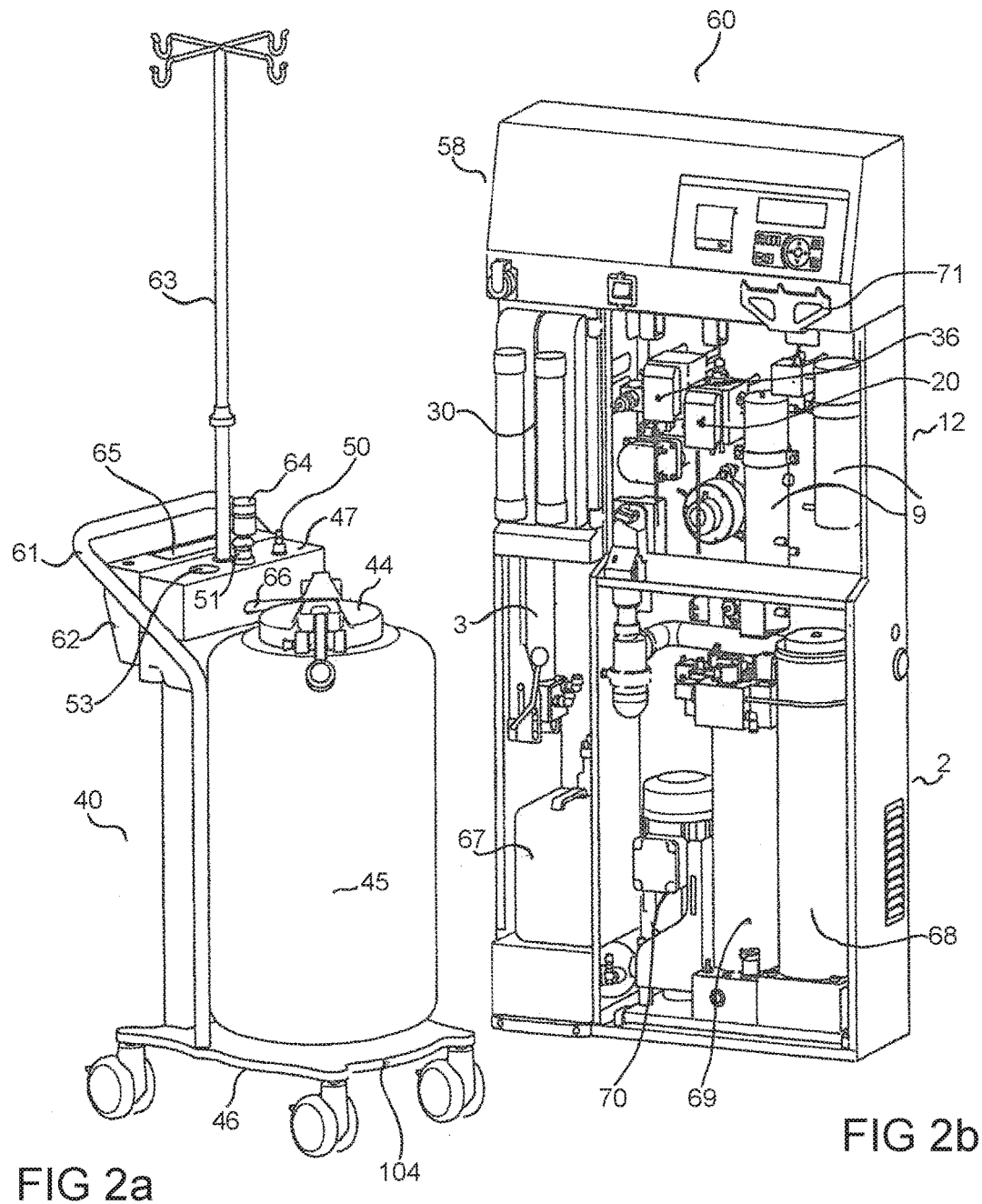
FIG. 2a is a view of a mobile flush solution container.
FIG. 2b is a view of a filling station.

FIG. 1 shows the entire preparation up to the point of application. The fluid to be prepared can be forwarded to the RO system (2) via, for example, optional preliminary filtration (1), which can be formed as particle and/or further filtering stages for the elimination of hardeners and chlorine.

For the elimination of microbiological contamination, the RO system (2) contains, for example, a disinfection unit (4) with which chemothermal disinfection can be conducted without the involvement of the user. Canister (67) contains the disinfecting/cleaning agent that is used with advantage as a citrate-containing solution. The further function of mechanism (4) is derived from the depiction and is not further described here. Naturally hot cleaning of the RO system without the use of further disinfecting agents is possible.

The permeate created by the RO system (2) is circulated over the primary side of the filter (3). The permeate released by the RO controller (58) by means of non-depicted conductivity measurement reaches the secondary side of the filter (3) and then the mixing unit (12) via permeate release valve (5).

Permeate possibly already preheated by the RO system (2) is heated to the required flush solution temperature via the heater (9) and temperature regulator (8, 13). The permeate is supplied via line (11) to a mixing chamber (15) into which concentrate from bag (26) and line (25), the connector (24) and device-side link connector (22) is supplied by means of pump (23).

The concentrate flap (20) is thereby opened, detector (19) reports "open" because magnet (21) has exceeded the required distance. The concentrate flush valve (17) is only opened when the flap (20) is closed and with correspondingly selected or preset flush programs in order to clean the link connector (22).

Concentrate bag (26), with its hangers (27), is hung into the corresponding hooks of the concentrate bag scale (28).

The second conductivity and temperature measurement (16) detects the corresponding values for reasons of redundancy. The flush fluid that has been homogeneously mixed and tempered by the chamber (15) reaches a second sterile filter (30) via line (29).

Incorrect flush fluid is discarded to the drain (100) via the bypass valve (31).

With the valve (31) closed and the flush solution release valve (33) open, the flush fluid is directed via the device-side flush solution connector (35), the bag connector (38) connected thereto, line (39), to the mobile flush solution container (40) into which a sterile flush solution bag (82) is loaded. The possibility to remove a flush solution sample volume exists at the sampling point (32).

The mobile flush solution container contains a scale (43) that registers the respective filling level or the weight of the flush volume. Likewise a thermal sensor (59) is affixed in such a manner that the flush fluid temperature can be indirectly measured.

With the flush solution flap (36) closed and the selection and initiation of a corresponding flush program, the device-side connector (35) is flushed or disinfected with sterile fluid or cleaning solution, respectively, via flush drain (99).

The test of the filters (3/30) takes place with closed flaps (20/36) by feeding filtered air by means of air pump (6) and can selectively expose the secondary side of the filter (3) or the primary side of the filter (30) to air by means of a valve switch. The fluid is thereby partially displaced by the air. Due to the hydrophilic character of the filter membrane, given intact filter characteristics, only a very slight pressure drop will result which can be registered or monitored, as the case may be, by means of pressure sensor (14) and electronics (58).

This test can be used to verify or check, as the case may be, both the filters (3/30) and also the tightness of the flaps (20, 36).

FIG. 1 likewise schematically depicts a possible transfer of the flush fluid to an endoscopic system (57). Compressed air connector (48) can be linked to an in-house compressed gas source by means of flexible hose lines (49).

To guarantee a constant flush fluid flow, the pressure regulation unit (47) includes an adjustable pressure regulator (50), an emergency-off with mushroom button and forced venting (51), a manual pressure limiting valve (52), a manometer display (53), and an electronic pressure sensor (54) that, like all sensors and actuators, can be evaluated and depicted by means of redundant electronics (58).

The low-pressure regulating valve (50) is adjustable. The pressure regulation unit (47) can be designed for a regulation range from 0 to 0.5 bar and is adjusted for practical use to 0.3 bar feed pressure, for example, for prostate gland operations. The air regulated in this way is introduced into the pressurized container (45) via hose connection (66).

The flush fluid in bag (41/82) is conveyed by the fed pressure via transfer link (55) and a suitable transition system (56) to the endoscopic system (57).

It shall be understood that units other than endoscopic systems can also be linked to system (56).

For the sake of completion, it is ascertained that a further sterile filter, not depicted here, would be connectable to line (55).

Likewise it would be possible to introduce the regulated compressed gas medium directly into the flush solution bag (41).

FIG. 2 is a three-dimensional illustration of the complete unit of a mixing system and filling station. On the basis of the assumed spatially confined conditions in hospitals, the filling station (60) was designed to be as flat as possible in order not to interfere with the passageways in corridors or in rooms. This requires a vertical construction of the RO system (2) with membrane (68), feed tank (69) and pump (70). Also depicted is a cleaning canister (67).

The mixing unit (12) is affixed above the RO system, whereby in this drawing only the positions of the concentrate flap (20), the flush solution flap (36), the heater (9) and the sterile filter (30) are indicated in order to illustrate the handling, whereby the flaps are depicted here in the closed state.

Concentrate bag scale (28) is mounted underneath the electronics (58) and is depicted in the form of an extension piece (71) with holding hook for the concentrate bag.

Installation is flush with the wall at a suitable location at a corresponding height above the floor in order to guarantee communication, as later explained, and cleaning.

The mobile flush solution container (40) consists of a transport carriage (46) with push and pull handle (61), the pressurized container (45), a lid (44) and an infusion pole (63).

Constituents of the mobile flush solution container (40) are a pressure regulation unit (47), whose outlet discharges directly into the pressurized container (45) via a flexible hose connection (66), and electronics (62) with a communication display (65), for example, for the display of the filling level, temperature, compressed air and other relevant values, and a display light (64).

Communication between the flush solution container (40) and filling station (60) is effected wirelessly by means of sensors in the roller area underneath the bottom plate (104) of the transport carriage (40).

The detection of the park or docking positions of the flush solution container (40) at the filling station (60) is given by the position of the preferably infrared sensors.

On the filling station side, a corresponding sensor is affixed at the same level. The docking angle and docking position at the filling station are thereby to be influenced by the selection and position of the sensors.

The mobile flush solution container (40) can be equipped with a rechargeable battery and/or a power supply; likewise isolation and/or the addition of a heating unit preferably as heating foil is possible for heating or loss-free storage of the heated flush fluid. The addition of an internal compressor as a pressure source is likewise possible and practicable. Other shapes, e.g., prismatic, can also be used.

The further components are explained to some extent from the depiction or are explained later. It shall be understood that shown here is a space-saving construction of the components whose arrangement can differ from that depicted and that is also conceivable in other embodiments.

Likewise the labeling has not been referenced in all points.

Figure 3A:
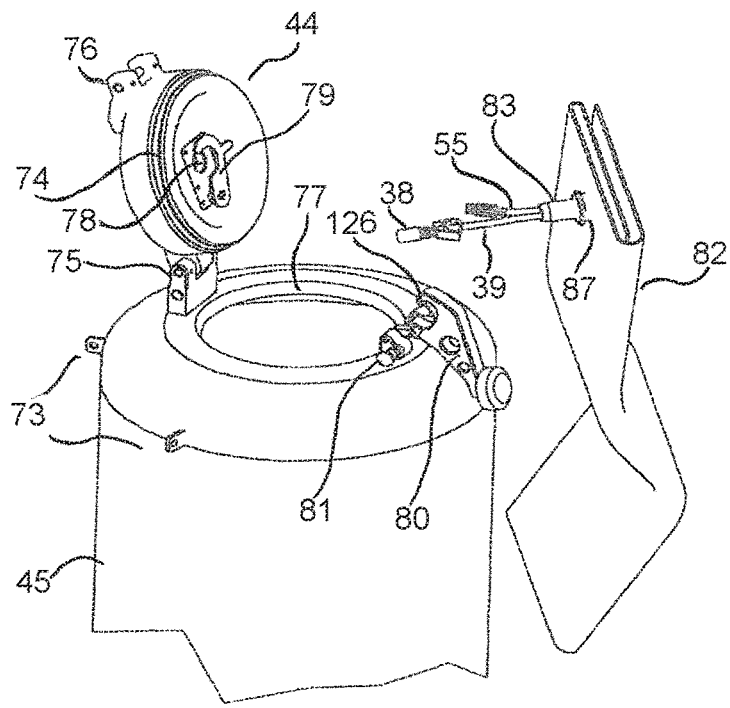
FIG. 3a is a view of a pressurized container with an open lid.
Figure 3B:
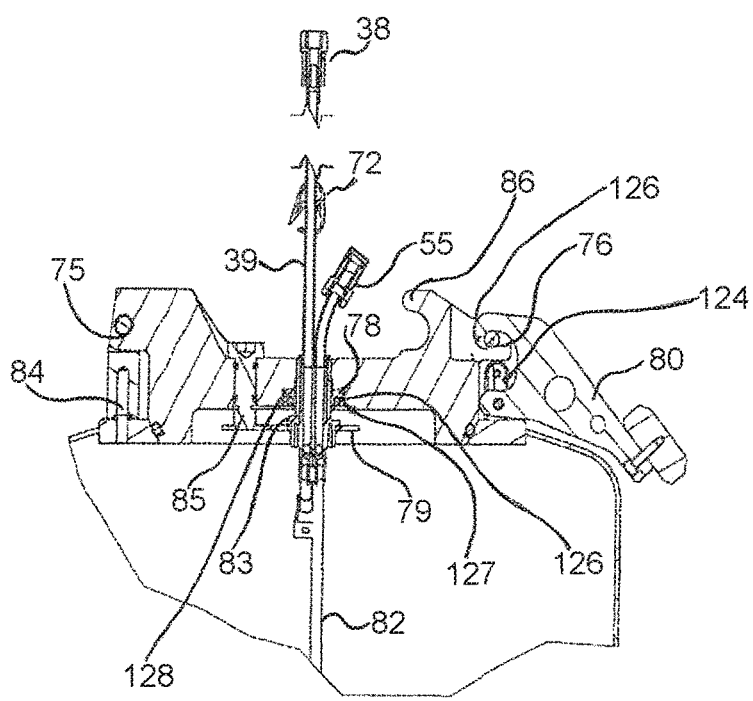
FIG. 3b is a partial cross-sectional view of the container with the lid closed.

FIG. 3 schematically shows the pressurized container (45) with open lid (44) and a connector receptacle (78), through which the cylindrical bag connector (83) is inserted and held by means of movable connector locking device (79) and holding slot (87).

In order for a positive sealing with good sliding properties to be possible between the connector (83) and connector receptacle seal (78), preferably the seal (78) consists of a Teflon insert (128), which is pressed with an O-ring (126) and a pressure plate (127) against connector (83) in such a manner that the aforementioned objectives are achieved.

A positive and sealing joining of the lid (44) to the pressurized container (45) is achieved on the one hand by lid seal (74) and the conical seal mounting (77) in the pressurized container opening in the closed state.

For closing, hook (126) pulls the lid locking device (76) into position by means of locking device handle (80). Locking device safeguard (81) thereby locks in place behind the pivot joint (124). Lid clamping hinge (75) holds lid (44) in the open state in an upright position.

It shall be understood that the bag (82) is to be introduced into the container for this purpose For vertical support, two lateral guides (73) are affixed to the pressurized container (45).

The compressed air supply (66) is affixed, for example, in the hinge area (75) by means of link (84).

Connector locking device (79) is to open from outside via a turning shaft (85) by means of a tool in the event of an error.

Likewise, in this figure the filling line (39) is depicted with connector (38), whereby said filling line is to be connected to the link (35) in the filling process. Clamp (72) can be closed after the filling process. For differentiation between the filling line (39) and the transfer line (55), these are equipped with different connectors and executed, as depicted, in different lengths.

FIG. 4 offers a perspective schematic view of the flush solution flap (36), whose opening, closing and excavation and cleaning process are described in the following.

Located in the flap (36) is a magnet (37) that activates a magnetic contact (34) when the flap is closed.

For flushing, the flap (36) is closed so that the flap locking device hook (91) snaps the flap locking device (89) into place in the locking collar (96) of the link connector (35).

By pressing back the locking device (89) over the pivot point (92) by means of flap locking device handle (90) the locking device spring (93) is compressed and the flap locking device hook (91) thereby releases the excavation process of the flap (36). The flap swivels upwards. This is supported by an excavation spring (102) which engages at the side of the flap pivot point (101).

For complete flushing of the connector (35), the seal (94) presses in a positive fit onto the outer cone (95) of the connector (35) when the flap is closed.

Via link (29) via the internal cone (88) the flush fluid penetrates to the flushing area (103) and from there via the circumferentially arranged flush bores (98) of the connector (35) into the annular gap (97) from which the flush drain (99) procedure takes place.

To rule out mix-ups during use, the technical execution of the flush solution links was designed to be different than those for the concentrate links.

Located under the flush solution flap (36) is a flush solution connector (35) executed, for example, with an internal cone (88) 1 to 16 and a double-threaded external screw thread 13×8. Located on the flush solution bag (41), which is executed as a disposable article, is the filling line (39) with disposable connector (38) which as a male connector is equipped, for example, with freely rotatable union nut with internal screw thread 13×8 and an internal outer cone 1 to 16 in such a way that in the coupled state a positive, sealing joining is guaranteed by the two cones and screw thread. A hose clip (72) can be mounted in the filling line (39).

FIGS. 5 and 6 show further details of the transport carriage (40).

5a shows in perspective the overall assembly whose details have already been described in more detail in the preceding figures.

5b shows in a sectional view the upper lateral guide (73) of the pressurized container (45), which serves as the upper support with vertical leeway. Likewise depicted are a bottom drain (106), which is positioned in a bottom plate of the pressurized container (111) and the position of the temperature sensor (59).

5c depicts the mounting of the flush solution container scale (43) to the bottom plate (104) and pressurized container (111). The screws/bolts (108) are provided to secure the scale (43) against transport obstacles.

(109) shows the receptacle of the wireless communication sensor. (109) can, for example, be used as an infrared sensor or sensors with corresponding transparent housing.

A corresponding sensor is affixed at the same level on the filling station side. The docking angle and docking position at the filling station are thereby to be influenced by the selection and position of the sensors.

(107) shows the position of a scale test mechanism, which is described in more detail in FIG. 6.

The test mechanism (107) comprises a test weight (112), a limit stop bracket (113) and a lifting magnet (114). Limit stop bracket (113) is permanently affixed to pressurized container (45) and engages with a fork-shaped cut-out into opening (118). By triggering the lifting magnet (114), plunger (115) is pulled downwards, spring (116) is compressed so that test weight (112) with limit stop damping (122) presses with full weight against limit stop bracket (113) and consequently can be registered by the scale (43). After completion of the test process, lifting spring (116) presses test weight (122) upwards and consequently releases the limit stop bracket (113).

The screws (110) show the mounting of the scale cell (43) to the bottom plate (111) of the pressurized container and bottom plate of the mobile transport carriage (104). Via this connection, the pressurized container has a more or less floating mounting above the scale cell (43) on the chassis or on its bottom plate (104). The upper support with vertical leeway is provided by means of holder (73).

The locking device (81) of the locking device handle (80) is again illustrated elsewhere in the figure. The locking device handle (80) is mounted by means of pivot joint (124) to pivot point (123). During the closing process, pivot joint (124) with chamfer (125) is swiveled past locking device bolt (81) that is pretensioned by means of a spring. During the locking process, (81) is pressed into a pretensioned position and, in the fully closed state of the lid (44), it snaps into place behind the pivot joint (124).

LEGEND

1. Preliminary filtration
2. RO system
3. Permeate ultra/sterile filter
4. Disinfection unit
5. Permeate release valve
6. Air pressure infeed, air pump
7. Air intake filter
8. Temperature regulator
9. Heater
10. Overtemperature protection
11. Permeate supply line -continued 12. Mixing unit
13. Temperature regulator/-display
14. Pressure sensor
15. Mixing chamber
16. Redundant conductivity measurement/temperature display
17. Concentrate flush valve
18. Flush line
19. Concentrate flap detector
20. Concentrate flap
21. Magnet
22. Concentrate bag link connector with double-threaded internal screw thread and internal outer cone
23. Concentrate pump
24. Concentrate bag connector with breaking cone with double-thread external screw thread and internal cone
25. Concentrate bag link
26. Concentrate bag
27. Concentrate bag hanger
28. Concentrate bag scale
29. Flush solution line
30. Sterile filter 2
31. Flush solution by-pass valve
32. Sampling point
33. Flush solution release valve
34. Flush solution flap detector
35. Flush solution connector with internal cone and double-threaded external screw thread
36. Flush solution flap
37. Magnet
38. Flush solution bag connector with outer cone and internal screw thread
39. Flush solution filling line
40. Mobile flush solution container
41. Flush solution bag
42.
43. Flush solution container scale
44. Lid
45. Pressurized container
46. Transport carriage
47. Pressure regulation unit
48. Compressed air connector
49. Hose extension
50. Pressure regulator
51. Emergency off
52. Pressure limiting valve
53. Pressure manometer
54. Pressure sensor
55. Transfer link with double-threaded external screw thread, internal cone and sealing flap
56. Transition system
57. OP application
58. Electronics
59. Thermal sensor
60. Filling station
61. Push and pull handle
62. Electronics for transport carriage
63. Infusion pole
64. Signal light display
65. Communication display for pressure, temperature, filling level
66. Compressed air hose connection
67. Disinfecting/cleaning agent canister
68. RO membrane
69. Feed tank
70. Pump with drive
71. Concentrate scale extension piece with bag hanging hook
72. Hose clip
73. Lateral guide for pressurized container
74. Lid seal
75. Lid clamping hinge
76. Lid locking device
77. Pressurized container opening with conical seal mounting
78. Connector receptacle with internal pre-stressed sliding seal
79. Connector locking device
80. Locking device handle with hook
81. Locking device safeguard
82. Flush solution bag
83. Bag connector
84. Compressed air supply
85. Turning shaft locking device with exterior hexagonal socket -continued 86. Excavation handle
87. Holding slot
88. Flush solution connector internal cone
89. Flap locking device
90. Flap locking device handle
91. Flap locking device hook
92. Flap locking device pivot point
93. Flap locking device spring
94. Flap seal
95. Seal counter-bearing
96. Locking collar
97. Flush flow annular gap
98. Flush bores
99. Flush drain
100. Drain
101. Flush solution flap turning shaft
102. Excavation spring
103. Flushing area
104. Bottom plate of mobile flush solution container
105. Rollers
106. Drain
107. Scale test mechanism
108. Bumper
109. Wireless communication
110. Mounting screws for pressurized container/scale
111. Pressurized container bottom plate
112. Test weight
113. Limit stop bracket with fork-shaped receiving element for test weight
114. Lifting magnet
115. Lifting magnet plunger
116. Lifting spring for test weight
117. Test weight guide
118. Opening for limit stop bracket
119. Counter bearing for lifting spring
120. Test weight support bolt
121. Support bolt damping rubber
122. Limit stop damping
123. Pivot point for pivot joint
124. Pivot joint
125. Chamfer, pivot joint
126. O-ring
127. Pressure plate
128. Teflon insert

The invention claimed is:

1. A mobile flush solution container with a transport carriage and a pressurized container into which a pressurized gas can be introduced in order to deliver flush solution from the pressurized container, characterized in that the flush solution is received in a flexible flush solution bag (82) that is arranged in the pressurized container (45), in that the pressurized container (45) has a lid (44) with a connector receptacle (78) through which a bag connector (83) that is non-detachably connected to the flush solution bag (82) can be tightly guided and locked in the lid (44), in that running through the bag connector (83) is a flush solution filling line (39), in that the transport carriage (40) has a container scale (43) on which the pressurized container (45) lies, wherein the pressurized container (45) is disposed above the container scale, in that the transport carriage (40) has a pressure regulation unit (47) for a pressure in the pressurized container (45), in that affixed to the pressurized container is a bracket (113), and in that arranged on the transport carriage (40) is a test weight (112) and a lifting spring (116) for selectively positioning the test weight onto the bracket, wherein upon a test signal the test weight can be automatically connected to the pressurized container in order to increase a weight of the pressurized container by the weight of the test weight.

2. The mobile flush solution container according to claim 1, characterized in that
the container scale (43) is affixed on a bottom plate (104) of the transport carriage (40) and on a bottom plate (111) of the pressurized container (45).

3. The mobile flush solution container according to claim 1, characterized in that
mounted on the transport carriage (40) is an infusion pole (63).

4. The mobile flush solution container according to claim 1, characterized in that
furthermore running through the bag connector (83) is a transfer line (55) for connection to a transition system (56);
wherein a fluid path of the transfer line is a separate path from a fluid path of the flush solution filling line.

5. The mobile flush solution container according to claim 4, characterized in that
the flush solution filling line (39) and the transfer line (55) are equipped with different connectors, which are disposed along the fluid path of the flush solution filling line and the fluid path of the transfer line, respectively.

6. The mobile flush solution container according to claim 1, characterized in that
the transport carriage (40) has a pressure monitoring unit for the pressure in the container (45).

\* \* \* \* \*